United States Patent [19]

Gander et al.

[11] Patent Number: 5,648,096
[45] Date of Patent: Jul. 15, 1997

[54] PROCESS FOR THE PRODUCTION OF MICROCAPSULES

[75] Inventors: Bruno Gander, Immensee; Hans Peter Merkle, Zürich, both of Switzerland

[73] Assignee: Schwarz Pharma AG, Monheim, Germany

[21] Appl. No.: 264,007

[22] Filed: Jun. 22, 1994

Related U.S. Application Data

[63] Continuation of PCT/CH93/00246, Oct. 18, 1993, published as WO94/09898, May 11, 1994, abandoned.

[30] Foreign Application Priority Data

Oct. 26, 1992 [CH] Switzerland ............... 3319/92

[51] Int. Cl.$^6$ .................... A61K 9/14; A61K 9/16; A61K 9/50
[52] U.S. Cl. ................ 424/489; 424/490; 424/491; 424/492; 424/493; 424/494; 424/495; 424/496; 424/497; 424/498; 424/457; 424/499; 424/500; 424/501; 424/502; 430/138
[58] Field of Search .................... 424/489, 491, 424/499, 457, 490, 492–498, 500, 502; 430/138

[56] References Cited

U.S. PATENT DOCUMENTS

| | | | |
|---|---|---|---|
| 4,637,905 | 1/1987 | Gardner | 264/4.3 |
| 5,066,436 | 11/1991 | Komen et al. | 264/4.3 |
| 5,354,556 | 10/1994 | Sparks et al. | 424/419 |
| 5,366,733 | 11/1994 | Brizzolara et al. | 424/426 |

FOREIGN PATENT DOCUMENTS

| | | |
|---|---|---|
| 0 102 265 A3 | 3/1984 | European Pat. Off. . |
| 0 315 875 A1 | 11/1987 | European Pat. Off. . |
| 0 330 180 A1 | 8/1989 | European Pat. Off. . |
| 0 505 966 A1 | 2/1992 | European Pat. Off. . |
| 4247987 | 9/1992 | Japan . |

OTHER PUBLICATIONS

Derwent Abstract, Accession No. 85-1 30922, Kato 1985.
Nakano et al. Internation J. of Pharmaceutics 4: 291–298 (1980).
Japanese Abstract (see above).
Abstract, Derwent Publications Ltd., London, GB, AN 85–130922 & JP, A, 60 067 417 (KATOH) 17 Apr. 1985.
Bodmeier et al., *Preparation of Biodegradable Poly±lactide Microparticles Using a Spray–Drying Technique*, J. Pharm. Pharmacol. 1988, 40:754–757.
Lewis, *Controlled Release of Bioactive Agents from Lactide/Glycolide Polymers*, Biodegradable Polymers as Drug Delivery Systems, pp. 1–41.
Spenlehauer et al., *In Vitro and in Vivo degradation of Poly(D,L lactide/glycolide)Type Microspheres Made by Solvent Evaporation Method*, Biomaterials, vol. 10, No. 8, Oct. 1989, pp. 557–563.
Wang et al., *Degradation of poly(ester) microspheres*, Biomaterials, vol. 11, No. 9, Nov. 1990, pp. 679–685.
Jailil et al., *Biodegradable poly(lactic acid)and poly(lactide–co–glucolide) Microcapsules: Problems Associated with Preparative Techniques and Release Properties*, J. Microencapsulation, 1990, vol. &, No. 3, pp. 297–325.

*Primary Examiner*—James C. Housel
*Assistant Examiner*—Jennifer Shaver
*Attorney, Agent, or Firm*—Merchant, Gould, Smith, Edell, Welter & Schmidt

[57] ABSTRACT

A method for the production of microcapsules embedded with pharmaceuticals, peptides, proteins, enzymes and vaccines, which uses biodegradable solvents, and microcapsules free of toxic residual solvents is described. The microcapsules are obtained by spraying of a solution, suspension or water-in-oil dispersion of active materials and biodegradable polymers.

24 Claims, 1 Drawing Sheet

PROCESS FOR THE PRODUCTION OF MICROCAPSULES

CROSS-REFERENCE TO RELATED APPLICATION

This is a continuation of International Application PCT/CH93/00246, with an international filing date of Oct. 18, 1993, now abandoned.

The present invention concerns a process for the production of biodegradable microcapsules employing biodegradable and toxicologically harmless solvents. The term, microcapsule, used, for simplicity's sake, includes actual microcapsules as well as microspheres and microparticles according to the following definitions: The term microcapsule describes spherical particles in the size range 1–1,000 µm, consisting of an internal nucleus, which contains the active material in liquid or solid form, and the capsule wall consisting of polymer. The terms microspheres or microparticles describe spherical and non-spherical particles in the size range of 1–1,000 µm, consisting of a polymer matrix, in which the active material is imbedded as a so-called solid solution or suspension.

BACKGROUND OF THE INVENTION

Biologically highly sensitive active materials such as certain pharmaceuticals, peptides, proteins, enzymes and vaccines are preferably used parenterally as injection solutions. Many of these active materials have a short biological half-life or are not very active when applied in solution (vaccines). This means, that a continuous or pulse-like release of active material (long term release) represents an unavoidable prerequisite for a successful therapeutic or preventive treatment. Such prolonged release of active material can be achieved through incorporating the active material, for example, into a biodegradable release system. Such release systems can be produced in the form of microcapsules or implant rods. Biodegradable microcapsules have proved to be especially useful in the past, because these particles can be easily administered parenterally with common injection needles. Known biodegradable pharmaceutical release systems are based on polyesters of lactic acid and glycolic acid (D. H. Lewis, Controlled release of bioactive agents from lactide/glycolide polymers, in: Biodegradable polymers as drug delivery systems, M. Chasin, and R. Langer (Eds.), M. Dekker, New York, 1990, pp. 1–41).

For the production of microcapsules from polyesters, such as poly(lactides) and poly(lactide-co-glycolides), three main processes are known: the coacervation (phase separation), e.g. through addition of a non-solvent, solvent evaporation, or solvent extraction from an oil-in-water dispersion, and spray drying (R. Jalil et al., J. of Micro-encapsulation 7,297–325, (1990)). Common to all of these processes is the requirement of an organic polymer solvent, which is removed again for the most part through the process. Because the complete removal of the solvent from the polymer is not possible, residual solvent always remains in the microcapsules, lying in the range of 0.01–10% (G. Spenlehauer et al., Biomaterials 10, 557–563, (1989)); D. H. Lewis et al., PCT WO 89/03678). The solvents mainly described until now for the three processes above are not biodegradable and in part are extremely toxic or environmentally harmful, e.g. methylene chloride, chloroform, benzene, tetrahydrofuran, acetonitrile, fluorochlorohydrocarbons and others, which compromise the advantages of these biodegradable release systems.

For illustration, according to the U.S. Pat. No. 5,066,436 microcapsules are produced through coacervation, which are contaminated with such organic solvents to a large extent. In addition to the polymer solvent, other organic solvents are used for the actual phase separation, for the hardening and washing of the microcapsules. Moreover, the microcapsules produced this way are relatively large and agglomerate easily during the production process which additionally aggravates the removal of residual solvent.

The disadvantages connected with the solvent evaporation or extraction methods lie in the previously mentioned toxicologically not completely harmless residual solvents of the microcapsules. On the other hand, these particular methods show the inherent difficulty that water soluble active materials such as certain pharmaceuticals, peptides, proteins, enzymes, and vaccines are lost through the aqueous dispersion phase and, therefore, escape partial or complete encapsulation.

Spray drying is a known, simple and quick process for the production of biodegradable microcapsules. The difficulty of producing spherical and not porous particles of the biodegradable lactic and glycolic acid polymers has been repeatedly pointed out. With the poly (D,L-lactic acid) dissolved in methylene chloride, very irregular microcapsules are obtained with an irregular surface and a high proportion of fibrous material (R. Bodmeier et al., J. Pharm. Pharmacol. 40, 754–757 (1988)). According to the European Patent Application A1 315,875 copolymers of lactic and glycolic acid (PLGA) cannot be processed into microcapsules via spray drying. These copolymers are, however especially interesting as matrix or wall material, because they break down more quickly in the organism than the pure homopolymers of lactic and glycolic acid. It has been described that the PLGA-polymers, especially PLGA composed of 50% of each lactic and glycolic acid (PLGA 50:50), give release of the active material over 3–4 weeks, which for example for hormonal and enzyme therapy represents a desirable dosing interval.

A further difficulty with spray drying for microencapsulation arises from the properties of the substance to be encapsulated. Substances, which are soluble in polymer solution (e.g. in methylene chloride), are usually built into microcapsules with relatively high efficiency and homogenous distribution (high 'content uniformity'). In contrast, the microencapsulation of substances which are insoluble in polymer solution is more difficult as for example for certain pharmaceuticals, peptides, proteins, enzymes and vaccines. If these active materials are suspended in the organic polymer solution in a micronized form, only an unsatisfactory incorporation efficiency is often achieved, which is strongly dependent on the fineness of the active material. For this reason, water soluble active materials are often first dissolved in water, and the aqueous solution of active material solution is then dispersed in the polymer solution (water-in-oil dispersion). With the common known solvents, only unsatisfactory water-in-oil dispersions can be produced which prove to have insufficient fineness and physical stability. The result is a quick coalescence of the dispersed, aqueous phase (coalescence), and connected with this, a poor encapsulation efficiency. For this reason, it has been repeatedly observed that micro-encapsulated protein is released within 1–3 days. This is traced back in general to a high proportion of insufficiently encapsulated active material and high microcapsule porosity (H. T. Wang et al., Biomaterials, 11, 679–685 (1990)). In addition, water miscible solvents such as acetone, tetrahydrofuran, dioxane, acetonitrile and other cannot be used because this miscibility may lead to precipitation or aggregation of the active material and/or the polymer.

SUMMARY OF THE INVENTION

The present invention solves the above problems by manufacturing microcapsules using a method which employs biodegradable and toxic-free materials.

Accordingly, the present invention is a method of manufacturing microcapsules containing one or more biodegradable polymers and at least one active material, which method comprises:

(a) dissolving the biodegradable polymer(s) in a biodegradable solvent;

(b) mixing the active material in a biodegradable solvent or aqueous medium;

(c) combining components (a) and (b), and (d) spray drying the resulting mixture.

Essential to the invention is the use of biodegradable solvents, whereby the microcapsules manufactured with them are free of toxic residual solvents. The microcapsules are obtained by spraying of a solution, suspension or dispersion of active materials and polymers. Water soluble as well as water insoluble biologically active substances are suitable for active materials to be imbedded. Water soluble active materials like peptides, proteins, vaccines preferably are dispersed as aqueous solutions in the polymer solution. Hereby a process is available, which is applicable in the production of pharmaceutical, vaccine and enzyme preparations.

DETAILED DESCRIPTION

Figure 1:
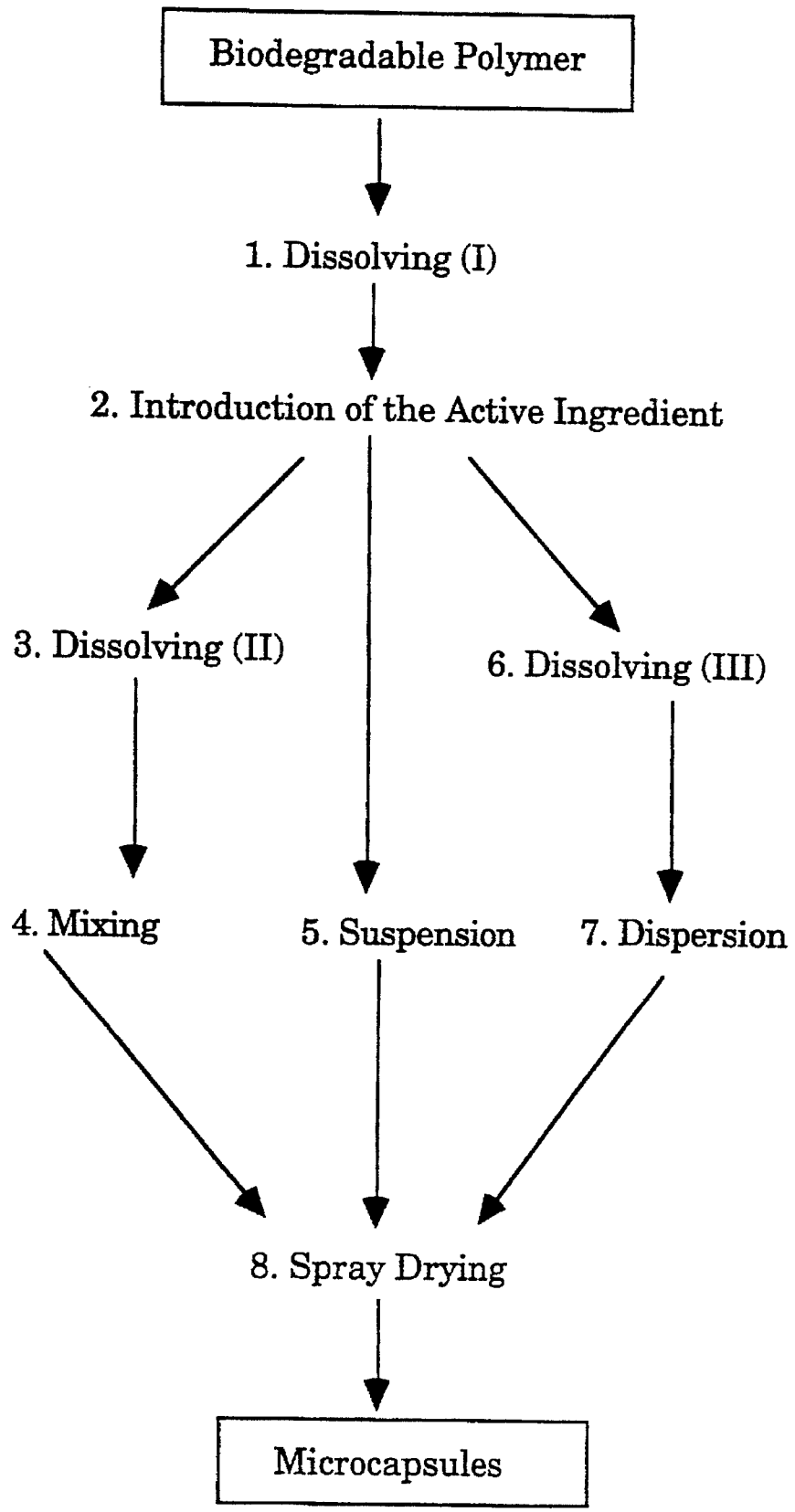
FIG. 1 shows the flow diagram for a process for the production of microcapsules of the present invention.

The following is a detailed description of the embodiments of the present invention including a best mode. Each operation is separately described as shown in FIG. 1.

1. Dissolving (I)

Starting point for the process are all biodegradable polymers, as far as they are soluble in the solvents according to the invention, like mono- and co-polyesters of the lactic, glycolic, and β-hydroxybutyric acids, as well as δ-valerolactone and ε-caprolactones. Polylactic and polyglycolic acid are also termed poly (lactides) and poly (glycolides). The dissolving of biodegradable polymers, or a mixture of biodegradable polymers, takes place in the solvents according to the invention, whereby a polymer solution (first solution) is generated. To these solvents belong the group of simple esters, consisting of a $C_1$–$C_5$ alcohol and a $C_1$–$C_5$-monocarboxylic acid, and mixtures of these simple esters with a $C_1$–$C_5$-alcohol. To these biodegradable solvents belong for example ethyl formate, propyl formate, butyl formate, ethyl acetate, propyl acetate, isopropyl acetate, ethyl propionate, ethyl butyrate, and ethyl valerate, and mixtures of these esters with ethanol, propanol, isopropanol and others. These solvents or solvent mixtures possess a surprisingly high solubility for biodegradable polyesters made, for example, of glycolic acid, lactic acid β-hydroxybutyric acid, δ-valerolactone and of ε-caprolactone. They are able to dissolve homopolymers as well as copolymers of these hydroxycarboxylic acids in a wide variation of molar ratios, for example 50:50, 65:35, 75:25 or 85:15, and over a wide range of molecular weights (2,000–150,000). The polymers can be brought into solution individually or as a mixture and the solvents according to the invention may be used individually or as solvent mixtures, made up of different esters or of esters and alcohols.

2. Embedding of the active material

The embedding of the active material to be encapsulated into the biodegradable polymer occurs in dependence of the active material's solubility in three different ways, corresponding to steps 3, 5 and 6. According to this invention, active materials are defined as substances which in living organisms, produce a biological effect, whereby this effect, for example, can be a pharmacological, an immunological, or enzymatic one. The active material to be encapsulated, in general, is in solid form (powder) but can also be in liquid form and can be processed as a liquid.

3. Dissolving (II)

Active materials, which are soluble in the biodegradable solvents according to the invention, consisting of esters, $C_1$–$C_5$-alcohols and any ester-alcohol mixture of these, are directly dissolved in these whereby an organic active material solution (second solution) is generated. This active material solution represents the preferred process step, because it can be manufactured with the least effort and is thermodynamically stable.

4. Mixing

Subsequently the polymer solution (first solution) and the organic active material solution (second solution) are combined and mixed, whereby the substrate 'solution' is obtained. The solvents described here are characterized by a high solubility for a large number of low-molecular active materials, like certain pharmaceuticals and peptides. This advantageous property of these solvents also makes it possible to dissolve the active material and the biodegradable polymer simultaneously, by using the same solvent or a combination of biodegradable solvents. The process is then continued with step 8.

5. Suspending

Active materials, which are neither sufficiently soluble in water nor in the solvents according to the invention, are suspended mechanically or by means of ultrasound in the polymer solution, which contains the biodegradable solvents, whereby the substrate 'suspension' is obtained. To achieve a high incorporation efficiency, the active material is preferably suspended in a micronized form. Thereby, in general particles smaller than 10 µm are generally strived for. The process is then continued with step 8.

6. Dissolving (III)

Water-soluble active materials, like certain pharmaceuticals, peptides, proteins, enzymes, or vaccines, which cannot be dissolved in the solvents according to the invention, are preferably dissolved in an aqueous medium with as small a volume as possible, whereby an aqueous active material solution is generated. The aqueous medium can contain additives, as for example buffer salts, tensides, stabilizers and preservatives.

7. Dispersing

The aqueous active material solution obtained in step 6 subsequently is finely dispersed in the polymer solution, which contains the biodegradable polymer in the solvents according to the invention, whereby the substrate water-in-oil (W/O) dispersion is obtained. In this way, aqueous active material solutions up to a volume of 50% can be incorporated nanodispersedly into the polymer solution with little energy input. The dispersion can take place by means of simple shaking, but preferably by means of a mechanical dispersion tool or with ultrasound. The preferred dispersion method is ultrasound treatment with 50–400 W during 10–300 s or longer if necessary. These dispersions of aqueous active material solutions in polymer solution remain surprisingly stable over several hours (no coalescence) without addition of surfactants or pseudoemulsifiers and do not have to be continually dispersed during the spraying process, which is especially advantageous. The solvents according to the invention yield W/O-dispersions with aqueous active material solutions, which, with regards to fineness and stability, cannot be achieved with the solvents commonly used, as for example methylene chloride. The process is continued in step 8.

8. Spray Drying

The substrates obtained in steps 4, 5 and 7 'solvent', 'suspension' and 'W/O-dispersions' respectfully, are processed into microcapsules by spray drying which, for example, can take place with a Mini Spray Dryer 190 (Büchi). Microcapsules manufactured by spray drying generally have a diameter of 1–50 µm, but maximally 100 µm, and thus can easily pass through an injection needle. The degree of loading of the microcapsules (active material content) is between 0–50%, but preferably between 0–20%.

Microcapsules manufactured in this way are processed further in the appropriate manner and in accordance with the final use where for example a washing process, a fractionation into different particle sizes, a final drying under high-vacuum, a sterilization by means of γ-radiation or further processing can follow as desired.

The process described here in steps 1–8 allows to encapsulate active materials with differing solubility characteristics of a high incorporation efficiency and with a homogenous distribution in the polymer, because of the high dissolving capability of the solvents according to the invention for many active materials and because of the simple dispersibility of aqueous active material solutions. Depending on the polymer used, the degree of loading and the use of additives (release regulators), the active material is released from the microcapsule over a time period from 1 day to 1 year.

In contrast to the commonly used halogenated and non-halogenated organic solvents, the biodegradable solvents enable to produce microcapsules by spray drying even with poly (D,L-lactic acid) or poly (lactic-co-glycolic acid). The obtained products exhibit a regular spherical particle morphology and a smooth non-porous surface. Particle conglutination, agglomeration, or deformation are seldom seen.

The solvents according to the invention have, in addition, the extraordinary advantage that they are toxicologically harmless. Just as the polymers, which are the basis of the microcapsules, the solvents according to the invention, break down in the organism into smaller, non-toxic, and in part physiological components. This decomposition occurs mainly through hydrolysis, but can also be enzymatic, for example occurring by means of esterases or dehydrogenases. Contrary to the solvents according to the invention, the commonly employed solvents are transformed in the organism into toxic metabolites. Methylene chloride, for example, is metabolized in the organism into the respiratory poison carbon monoxide and into compounds with carcinogenic potential and varying toxicological effects.

The following list is illustrative but not exhaustive of the active materials which may be contained in the biodegradable microcapsules prepared by the present invention:

A. Low molecular weight active materials such as psychotropics, neuroleptics, e.g. promethazine, promazine, chlorpromazine, triflupromazine, alimemazine, levomepromazine, thioridazine, sulforidazine, periciazine, perazine, trifluperazine, perphenazine, fluphenazine, dixyrazine, prothipendyl, chlorprothixen, clopenthixol, flupentixol, melperone, haloperidol, bromperidol, trifluperidol, pipamperone, benperidol, fluspirilen, pimozide, sulpiride; antidepressants, (monoamine oxidase (MAO) inhibitors), e.g. imipramine, desipramine, trimipramine, lofepramine, clomipramine, opipramol, amitryptiline/-oxide, nortriptyline, protriptyline, dibenzepine, doxepin, melitracen, mianserin, maprotilin, (nomifensin), trazodone, viloxazin; tranquilizers (therapeutic use: as anxiolytic sedatives), e.g. (-meprobamate), benzodiazepine, e.g. diazepam, prazepam, oxazepam, lorazepam, clonazepam, bromazepam, alprazolam; nootropic drugs, e.g. piracetam, pyritinol, meclofenoxate; opioid antagonists, e.g. naloxone, nalorphin, levallorphan, and opioid analgesics, e.g. morphine, hydromorphone, oxycodone, pethidin, levomethandone, dextromoramide, pentazozine, buprenorphin, tilidine, tramadol, fentanyl, alfentanil.

B. Nonsteroidal antiinflammatory drugs (NSAID) therapeutic use: rheumatic diseases, e.g. indomethacin, acemetacin, sulindac, tolmetin, diclofenac, lonazolac, ibuprofen, flurbiprofen, fenoprofen, ketoprofen, naproxen, pirprofen, indoprofen, carprofen, thiaprofen carboxylic acid, piroxicam, isoxicam; antiepileptics, e.g. phenobarbital, primidone, phenytoin, ethosuccimide, carbamazepine, valproic acid; antiparkinson drugs, e.g. amantadine, benserazide, l-dopa, carbidopa, selegilin, biperiden, metixen, trihexyphenidyl; beta blockers, e.g. bupranolol, alprenolol, oxprenolol, penbutulol, metoprolol, betaxolol, atenolol, acebutolol, metipranolol, propranolol, nadolol, pindolol, mepindilol, bopindolol, carteolol, carazolol, timolol, sotalol, toliprolol; calcium channel blockers, e.g. isradipine, nifedipine, nitrendipine, nimodipine, verapamil, gallopamil, diltiazem, prenylamine, fendiline, flunarizine; angiotensin converting enzyme (ACE) inhibitors, e.g. captopril, moexipril, enalapril, fosinopril, ramipril, perindopril, lisinopril, quinapril; nitrates, e.g. ISDN, 5-ISM, pentaerytrithyltetranitrate, GTN; vasodilators, e.g. pentoxifylline, cinnarizine, bencyclan; prolactin inhibitors, e.g. bromocriptin, lisuride, metergoline, thyroid hormones, e.g. levothyroxine ($T_4$), liothyronin ($T_3$), and oral antidiabetics, e.g. carbutamide, tolbutamide, chlorpropamide, glymidine, glibornuride, glibenclamide, glipizide, gliquidone, glisoxepid.

C. Sex hormones (female/male)/anabolic steroids/hormone antagonists, e.g. estradiol, estradiolvalerate, estradiolbenzoate, estradiolcipionate, estradioldienatate, estradioldipropionate, estradiolenantate, estradiolphenylpropionate, estradiolpivalate, estradiolundecylenate, ethinylestradiol, estriol, mestranol, quinestrol, diethylstilbestrol, progesterone, norethindrone, desogestrel, dienogest, levonorgestrel, norgestrel, chlormadinone acetate, lynestrenol, allylestrenol, ethynodioldiacetate, medroxyprogesterone acetate, hydroxyprogesterone acetate, testosterone, testosterone propionate, testosterone undecanoate, meserolone, e.g. nandrolone decanoate, clostebol acetate, metenolone acetate, stanozolol, e.g. cyproterone acetate, flutamide, drostanolone propionate, testolactone, clomifen, cyclofenil, tamoxifen, estramustin, fosfestrol, chlorotrianisen, aminoglutethimide.

D. Antihistamines (as depot antiallergic agent for example for hay fever), e.g. terfenadine, astemizol, dimetinden, clemastin, pheniramine, dexchlorpheniramine, azatadine, oxatomide; serotonin antagonists, e.g. methysergide, cyproheptadine, pizotifen, ketanserin; prostaglandins/ prostacyclin, e.g. PGE1/2, PGF 2a, prostacycline; anticoagulants, e.g. acenocoumarol, phenprocoumone, warfarin, ASS; blood lipid regulating drugs, e.g. clofibrate, etofibrate, bezafibrate, fenofibrate, gemfibrozil, lovastatin, pravastatin; vitamins (fat-soluble, water-soluble), e.g. Vit. A, Vit. D, Vit. E, (-Vit. K), Vit. B1, Vit. B2, Vit. B6, Vit. B12, Vit. Bc, Vit. C, biotin; chemotherapeutic agents/antibiotics (sulfonamide/combinations, β-lactams, tetracycline, macrolide, aminoglycoside), e.g. sulfacarbamide, sulfafurazol, sulfisomidine, sulfadiazine/(tetroxoprim), sulfamethoxazol/(trimethoprim), sulfamethoxypyridazine, sulfamethoxydiazine, sulfaperin, sulfadimethoxin, sulfamethoxypyrazine, sulfaguanol, e.g. nalidixic acid, oxalinic acid, quinoxalinic acid, pipemidic acid, norfloxacin, ofloxacin, ciprofloxacin, benzylpenicillin, phenoxymethylpenicillin, propicillin, oxacillin, dicloxacillin, flucloxacillin, ampicillin, amoxicillin, epicillin, azlocillin, methacillin, piperacillin, apalcillin, carbenicillin, ticarcillin, temocillin, bacampicillin, cephalothin, cefaloridine, cefazoline, cefazedone, cefamandole, cefuroxime, cefotiam, cefoxitin, cefotetan, cefotaxime, ceftizoxime, cefmenoxime, ceftriaxone, ceftazidime, cefoperazone, cefsulodin, cephalexin, cefaclor, cefradine, cefadroxil, latamoxef, aztreonam, imipenem, cilastatin, tetracycline, oxytetracycline, demeclocycline, doxycycline, minocycline, rolitetracycline, erythromycin, streptomycin, clindamycin, neomycin, kanamycin A; antifungal agents, e.g. griseofulvin, amphotericin, ketoconazol, miconazol; chemotherapeutic agents (antimetabolities, antibiotics, hormone antagonists, sex hormones), e.g. methotrexate, mercaptopurine, fluorouracil, cytarabine, aclarubicin, daunorubicin, doxorubicin, dactinomycin, epirubicin, bleomycin; high molecular weight active materials, e.g. erythropoetin, LH-RH-analogs, nafarelin, triptorelin, leuprorelin, buserelin, goserelin, antide, ciclosporin (A), interferon, somatotropin, somatostatin and analogs, octreotide, lanreotide, vapreotide, calcitonin, CGRP (calcitonin gene related peptide), ANP (atrial natriuretic peptide), BNP (brain natriuretic peptide), EGF (epidermal growth factor), GLP (glucagon like peptide), heparin, hirudin, hirugen, superoxide dismutase, angiotensinase, medullipin II, HBGF1 (KHK); endorphins/ enkephalins, e.g. a,β,y-endorphin, dynorphin, met-enkephalin, leu-enkephalin, and vaccines, e.g. tetanus-toxoid-vaccine, diphteria-toxoid vaccine, influenza, hepatitis, poliomyelitis, measles, mumps, German measles, pertussis, FSME, cholera, typhus/paratyphus, and rabies.

The following are specific examples to illustrate the present invention and are not limiting thereon.

EXAMPLE 1

The production of microcapsules, containing a protein: 0.09 g bovine serum albumin (Fluka, CH-Buchs) have been dissolved in 2.16 g water. With the help of an ultrasonic generator the aqueous solution was dispersed in a solution of 3.0 g Poly(D,L-lactic acid)(Resomer R202, Boehringer Ingelheim) in 57.0 g propyl acetate. The dispersion took place under cooling with ice in an ultrasonic processor (Vibracell, VC375, Sonics and Materials, Danbury, Conn.) with an energy of 260 W during 2×30 s. This dispersion was sprayed in a laboratory spray dryer (Mini Spray Dryer, B üchi 190, Büchi Laboratories, CH-Flawil) under the following conditions: Inlet temperature: 55° C., spray flow: 400 scale units, aspirator: 15 scale units, spray speed: 2.4 ml/min.

The microcapsules arose as a white, free-flowing powder. Yield: 1.8 g (58% of the theoretical value), active material content: 2.9% (100% of the theoretical value).

EXAMPLE 2

The production of microcapsules, containing a protein: 0.09 g Bovine serum albumin were dissolved in 2.16 g water. The aqueous solution was dispersed with the aid of an ultrasonic generator (260 W during 30 s) in a solution of 3.0 g Poly(D,L-lactic acid) (Resomer R202, Boehringer Ingelheim) in 57.0 g ethyl acetate. Dispersion and spray drying took place under identical conditions as in Example 1. Yield: 1.6 g (52% of the theoretical value), active material: 2.9% (100% of the theoretical value).

EXAMPLE 3

The production of microcapsules, containing a vaccine: 0.100 g lyophilized tetanus toxoid was dissolved in 2.0 ml water. The aqueous solution was dispersed with the aid of an ultrasonic generator in a solution of 5.0 g Poly(D,L-lactic acid-co-glycolic acid)(Resomer RG502, Boehringer Ingelheim) in 100.0 g ethyl ester. The dispersion took place under ice cooling with an ultrasound energy of 210 W during 2×30 s. The dispersion was sprayed in a laboratory spray dryer under the following conditions: Inlet temperature: 55° C., spray flow: 500 scale units, aspirator: 17.5 scale units, spray speed: 2.4 ml/min.

The microcapsules arose as a white, free-flowing powder. Yield: 0.7 g 40% of the theoretical value), protein contents: 1.82%, equivalent to 93% of the theoretically determined active material contents.

EXAMPLE 4

The production of microcapsules, containing an enzyme: 15 mg peroxidase from horse-radish with an activity of 75.8 U/mg (Fluka, CH-Buchs) were dissolved in 0.6 ml water. The aqueous solution was dispersed by means of ultrasonics of 375 W during 30 s under cooling with ice in a solution of 1.5 g Poly(D,L-lactic acid)(Resomer R202, Boehringer Ingelheim) in 30.0 g ethyl formate. The dispersion was sprayed with a laboratory spray dryer under the following conditions: Inlet temperature: 47° C., spray flow: 450 scale units, aspirator: 17 scale units, spray speed: 1.6 ml/min.

The microcapsules arose as a white, free-flowing powder. Yield: 0.92 g (61% of the theoretical value), enzyme activity: 0.177 U/mg microcapsules, corresponding to 23.4% of the theoretically determined activity.

EXAMPLE 5

The production of microcapsules, containing a pharmaceutical: 30 mg prostaglandin E2 (Fluka, CH-Buchs) and 6.0 g poly(D,L-lactic acid-co-glycolic acid)(Resomer RG502, Boehringer Ingelheim) were dissolved separately in 60 g ethyl formate each. The combined solutions were sprayed under the following conditions: Inlet temperature: 45° C., spray flow: 420 scale units, aspirator: 15 scale units, spray speed: 2.4 ml/min.

The microcapsules arose as a white, free-flowing powder. Yield: 4.2 g (70% of the theoretical value), degree of loading: 4.99 µg/mg microcapsules (100% of theoretical value).

EXAMPLE 6

The production of microcapsules, containing a hormone: 25 g 17-beta-estradiol were dissolved in a mixture of 125 ml anhydrous ethanol and 312.5 ml ethyl acetate. 100 g Resomer RG503 (Boehringer Ingelheim) were dissolved in 812.5 ml ethyl formate. Both solutions were combined under stirring whereby a stable suspension was formed.

The suspension was sprayed in a mobile Minor Spray Dryer (Company NIRO AS, Copenhagen): Inlet temperature: 67° C., spray speed: 0.9 l/h.

The microcapsules arose as a white powder, containing discrete, spherical particles. Yield: 80 g (80% of the theoretical value); degree of loading: 70.2 µg/mg microcapsules (85.1% of the theoretical value).

EXAMPLE 7

The production of microcapsules containing a hormone: 10 g 17-beta-estradiol were dissolved in a mixture of 100 ml anhydrous ethanol and 250 ml ethyl acetate. 90 g Resomer RG752 (Boehringer Ingelheim) were dissolved in 650 ml ethyl formate. The two solutions were combined under stirring and sprayed in a mobile Minor Spray Dryer (Company NIRO AS, Copenhagen) under the following conditions: Inlet temperature: 70° C., spray speed: 0.9 l/h.

The microcapsules arose as a white powder, containing discrete, spherical particles. Yield: 100 g (85% of the theoretical value); degree of loading: 89.6 µg/mg microcapsules (89.6% of the theoretical value).

EXAMPLE 8

The production of microcapsules, containing a synthetic vaccine: 0.02 g of a synthetic protein, consisting of the peptide sequence 947–967 of the tetanus toxin and a B-cell epitope of the repetitive region of the circumsporozoide protein of Plasmodium berghei, were dissolved in water. The aqueous solution was dispersed with the aid of an ultrasonic generator in a solution of 2.0 g Poly(D,L-lactic acid-co-glycolic acid)(Resomer RG752, Boehringer Ingelheim) in 40.0 g ethyl formate. The dispersion took place under cooling with ice with an ultrasound energy of 210 W during 2×30 s. The dispersion was sprayed in a laboratory spray dryer under the following conditions: Inlet temperature: 50° C., spray flow: 450 scale units, aspirator: 14 scale units, spray speed: 2.6 ml/min.

The microcapsules arose as white, free-flowing powder. Yield: 1.12 g (56% of the theoretical value); protein contents: 0.66%, corresponding to 0.6% of the theoretically determined active material content.

What is claimed is:

1. A method of manufacturing microcapsules containing one or more biodegradable polymers and at least one active material, which method comprises:
   (a) dissolving the biodegradable polymer(s) in a non-toxic biodegradable solvent which is selected from esters of a $C_1$–$C_5$-alcohol and a $C_1$–$C_5$-monocarboxylic acid;
   (b) incorporating at least one active material into the solution of the biodegradable polymer(s) obtained in step (a) either in the form of a solution of said active material in said biodegradable solvent; or in the form of a micronized powder of said active material, or in the form of a solution of said active material in an aqueous medium, and
   (c) spray drying the solution, suspension or water-in-oil dispersion obtained in step (b).

2. The method of claim 1, wherein the biodegradable solvent is ethyl formate.

3. The method of claim 1, wherein the biodegradable solvent is ethyl acetate.

4. The method of claim 1, wherein the biodegradable solvent is isopropyl acetate.

5. The method of claim 1, wherein the active material is a biologically active substance.

6. The method of claim 1, wherein the biologically active substance is a pharmaceutical, a peptide, a protein, an enzyme or a vaccine.

7. The method of claim 5, wherein the biologically active substance is a pharmaceutical, a vaccine or an enzyme.

8. A microcapsule containing one or more biodegradable polymers and a biologically active substance as prepared by the method of claim 1.

9. The microcapsule of claim 8, wherein the biologically active substance is selected from a pharmaceutical, a peptide, a protein, an enzyme and a vaccine.

10. The microcapsule of claim 9, wherein the biologically active substance is a pharmaceutical, a vaccine or an enzyme.

11. A method of manufacturing microcapsules comprising:
   (a) dissolving one or more biodegradable polymers in a non-toxic biodegradable solvent which is selected from esters of a $C_1$–$C_5$-alcohol and a $C_1$–$C_5$-monocarboxylic acid to form a first solution;
   (b) dissolving an active material in a non-toxic biodegradable solvent which is selected from esters of a $C_1$–$C_5$-alcohol and a $C_1$–$C_5$-monocarboxylic acid to form a second solution;
   (c) combining the first solution with the second solution to obtain a substrate solution and,
   (d) spray drying the substrate solution.

12. The method of claim 11, wherein the biodegradable solvent is ethyl formate.

13. The method of claim 11, wherein the biodegradable solvent is ethyl acetate.

14. The method of claim 11, wherein the biodegradable solvent is isopropyl acetate.

15. A method of manufacturing microcapsules comprising:
   (a) dissolving one or more biodegradable polymers in a non-toxic biodegradable solvent which is selected from esters of a $C_1$–$C_5$-alcohol and a C–$C_5$-monocarboxylic acid to form a polymer solution;
   (b) suspending an active material mechanically or by means of ultrasound in the polymer solution to obtain a substrate suspension, and
   (c) spray drying the substrate suspension.

16. The method of claim 15, wherein the biodegradable solvent is ethyl formate.

17. The method of claim 15, wherein the biodegradable solvent is ethyl acetate.

18. The method of claim 15, wherein the biodegradable solvent is isopropyl acetate.

19. The method of claim 15, wherein the active material is in micronized form.

20. A method of manufacturing microcapsules comprising:
   (a) dissolving one or more biodegradable polymers in a non-toxic biodegradable solvent which is selected from esters of a $C_1$–$C_5$-alcohol and a $C_1$–$C_5$-monocarboxylic acid to form a polymer solution;

(b) dissolving an active material in an aqueous medium to form an aqueous active material solution;

(c) mixing the aqueous active material solution with the polymer solution mechanically or with ultrasound to obtain substrate water-in-oil dispersion, and (d) spray drying the substrate water-in-oil dispersion.

21. The method of claim 20, wherein the biodegradable solvent is ethyl formate.

22. The method of claim 20, wherein the biodegradable solvent is ethyl acetate.

23. The method of claim 20, wherein the biodegradable solvent is isopropyl acetate.

24. The method of claim 20, wherein the dispersion in step (c) is obtained with ultrasound.

* * * * *

UNITED STATES PATENT AND TRADEMARK OFFICE
CERTIFICATE OF CORRECTION

PATENT NO. : 5,648,096

DATED : July 15, 1997

INVENTOR(S) : Gander et al.

It is certified that error appears in the above-identified patent and that said Letters Patent is hereby corrected as shown below:

Col. 10, line 47 (claim 15), please delete "$C-C_5$" and substitute therefore --$C_1-C_5$--

Signed and Sealed this

Twenty-fourth Day of March, 1998

Attest:

BRUCE LEHMAN

Attesting Officer  Commissioner of Patents and Trademarks